US012611166B2

(12) United States Patent
Bakker et al.

(10) Patent No.: US 12,611,166 B2
(45) Date of Patent: Apr. 28, 2026

(54) INTRALUMINAL ULTRASOUND VESSEL SEGMENT IDENTIFICATION AND ASSOCIATED DEVICES, SYSTEMS, AND METHODS

(71) Applicants: KONINKLIJKE PHILIPS N.V., Eindhoven (NL); PHILIPS IMAGE GUIDED THERAPY CORPORATION, San Diego, CA (US)

(72) Inventors: Bart Jacob Bakker, Eindhoven (NL); Nili Karmon, Sacramento, CA (US)

(73) Assignees: PHILIPS IMAGE GUIDED THERAPY CORPORATION, San Diego, CA (US); KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/695,392

(22) PCT Filed: Sep. 26, 2022

(86) PCT No.: PCT/EP2022/076614
§ 371 (c)(1),
(2) Date: Mar. 26, 2024

(87) PCT Pub. No.: WO2023/052278
PCT Pub. Date: Apr. 6, 2023

(65) Prior Publication Data
US 2025/0228521 A1     Jul. 17, 2025

Related U.S. Application Data

(60) Provisional application No. 63/250,498, filed on Sep. 30, 2021.

(51) Int. Cl.
*A61B 8/08*     (2006.01)
*A61B 8/00*     (2006.01)
*A61B 8/12*     (2006.01)

(52) U.S. Cl.
CPC ............ *A61B 8/0891* (2013.01); *A61B 8/085* (2013.01); *A61B 8/12* (2013.01); *A61B 8/5223* (2013.01)

(58) Field of Classification Search
CPC ......... A61B 8/0891; A61B 8/085; A61B 8/12; A61B 8/5223
See application file for complete search history.

(56) References Cited

U.S. PATENT DOCUMENTS

| 6,200,268 B1 | 3/2001 | Vince |
| 6,381,350 B1 | 4/2002 | Klingensmith |
| | (Continued) | |

OTHER PUBLICATIONS

P. Ambrosini et al, "A Hidden Markov Model for 3D Catheter Tip Tracking With 2D X-ray Catheterization Sequence and 3D Rotational Angiography", IEEE Transactions on Medical Imaging, vol. 36, No. 3, pp. 757-768, Mar. 2017 (Year: 2017).*
(Continued)

*Primary Examiner* — Nyrobi Celestine

(57) ABSTRACT

An intraluminal ultrasound imaging system is provided, which includes a processor in communication with an intraluminal ultrasound imaging catheter. The processor is configured to receive an intraluminal ultrasound image associated with a first segment of the body lumen from which the image was captured, which includes depictions of the body lumen and a second body lumen. The processor receives a second image obtained while the intraluminal ultrasound imaging catheter is moving at a pullback speed within the body lumen. The second image also includes depictions of the body lumen and the second body lumen. The processor computes body lumen properties from each image, and determines a second segment of the body lumen for the second image, based on a model associated with the body lumen properties, and/or the pullback speed, and outputs an indication of the second segment to a display.

14 Claims, 9 Drawing Sheets

$V_i$: vein segment state
$A_i$: artery segment state
$S_t$: pullback speed

(56)            References Cited

U.S. PATENT DOCUMENTS

| | | | |
|---|---|---|---|
| 7,074,188 B2 | 7/2006 | Nair | |
| 7,175,597 B2 | 2/2007 | Vince | |
| 7,215,802 B2 | 5/2007 | Klingensmith | |
| 7,359,554 B2 | 4/2008 | Klingensmith | |
| 7,463,759 B2 | 12/2008 | Klingensmith | |
| 7,846,101 B2 | 12/2010 | Eberle | |
| 2006/0069317 A1* | 3/2006 | Horn | A61B 1/041 |
| | | | 600/102 |
| 2015/0257850 A1 | 9/2015 | Sakamoto | |
| 2016/0157787 A1* | 6/2016 | Merritt | A61B 5/02007 |
| | | | 600/481 |
| 2020/0129148 A1 | 4/2020 | Jenkins | |
| 2021/0045710 A1* | 2/2021 | Bedi | A61B 8/12 |
| 2021/0319558 A1* | 10/2021 | Min | A61K 49/04 |
| 2022/0008124 A1* | 1/2022 | Zheng | A61B 8/085 |
| 2024/0245465 A1* | 7/2024 | Jenkins | A61B 90/37 |

OTHER PUBLICATIONS

International Search Report and Written Opinion of PCT/EP2022/ 076614, dated Dec. 23, 2022.
Yang, Ji et al "IVUS-Net: An Intravascular Ultrasound Segmentation Network", 2018. arXiv:1806.03583v2.

* cited by examiner

IVC 220

Spine 310

Abdominal Aorta 320

CIV 240

360 (compression by artery on vein)

Common iliac artery 330

Hip bone/ilium 340

External iliac artery 350

EIV 260

360 (compression by artery on vein)

$V_t$: vein segment state
$A_t$: artery segment state
$S_t$: pullback speed

INTRALUMINAL ULTRASOUND VESSEL SEGMENT IDENTIFICATION AND ASSOCIATED DEVICES, SYSTEMS, AND METHODS

TECHNICAL FIELD

The subject matter described herein relates to a system for medical imaging. In particular, the present disclosure describes aspects related to acquisition, display, identification, and annotation of peripheral intravascular ultrasound or IVUS images. This system has particular but not exclusive utility for diagnosis and treatment of vascular diseases.

BACKGROUND

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels such as arteries or veins within the human body, determining the need for treatment, optimizing treatment, and/or assessing the effectiveness of a treatment.

Peripheral venous interventions use imaging techniques such as X-ray and intravascular ultrasound (IVUS) to locate and assess lesion sites, and to guide and check the placement of stents. A necessary part of this procedure is the identification of named vein segments (e.g. common iliac vein) in the IVUS and/or X-ray images. This is currently done by hand, often using a combination of X-ray and IVUS. Such manual identification may be tedious and error-prone. However, accurate labeling is important for auditing, reimbursement, recordkeeping, and optimal treatment planning.

The information included in this Background section of the specification, including any references cited herein and any description or discussion thereof, is included for technical reference purposes only and is not to be regarded as subject matter by which the scope of the disclosure is to be bound.

SUMMARY

The present disclosure relates to intraluminal imaging of patients with an intraluminal imaging device, and describes systems, devices, and methods for the automatic identification of blood vessel segments in a sequence of intraluminal images. This may reduce the need for X-ray images and manual segment identification. This automatic identification relies on landmarks that are identified from the intraluminal images by computer vision algorithms, which may for example include machine learning or other pattern recognition algorithms. These landmarks may then be evaluated by a probabilistic algorithm such as a Bayesian graph network, which matches them against a priori anatomical knowledge to identify the correct vein segment of each image frame.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an intraluminal ultrasound imaging system, including a processor circuit configured for communication with an intraluminal ultrasound imaging catheter, where the processor circuit is configured to: receive a first intraluminal ultrasound image obtained by the intraluminal ultrasound imaging catheter while the intraluminal ultrasound imaging catheter is positioned within a first body lumen of a patient, the first body lumen including a plurality of segments, where the first intraluminal ultrasound image is associated with a first segment of the plurality of segments, and where first intraluminal ultrasound image includes depictions of the first body lumen and a second body lumen, where the first body lumen includes a first set of first body lumen properties, where the second body lumen includes a first set of second body lumen properties; receive a second intraluminal ultrasound image obtained by the intraluminal ultrasound imaging catheter while the intraluminal ultrasound imaging catheter is moving at a pullback speed within the first body lumen of the patient, where the second intraluminal ultrasound image includes depictions of the first body lumen and the second body lumen; compute, based on the second intraluminal ultrasound image, a second set of first body lumen properties and a second set of second body lumen properties; determine a second segment of the plurality of segments associated with the second intraluminal ultrasound image based on a model, where the model is associated with at least one of the first set of first body lumen properties, the first set of second body lumen properties, the second set of first body lumen properties, the second set of second body lumen properties, or the pullback speed; and output an indication of the second segment to a display in communication with the processor circuit. Other embodiments of this aspect include corresponding computer systems, apparatus, and computer programs recorded on one or more computer storage devices, each configured to perform the actions of the methods.

Implementations may include one or more of the following features. In some embodiments, the first body lumen comprises a plurality of subsegments, the first intraluminal ultrasound image is associated with first subsegment of the plurality of subsegments, and wherein the processor circuit is further configured to: determine a subsegment of the plurality of subsegments associated with the second intraluminal ultrasound image based on the model, and output an indication of the second subsegment to a display in communication with the processor circuit. In some embodiments, the processor circuit is further configured to display, on a display device in communication with the processor circuit, a schematic view of the first body lumen of the patient, where the schematic view includes: the plurality of segments and subsegments; and a visual indication of the second segment and second subsegment. In some embodiments, the model includes a state transition matrix. In some embodiments, the model includes at least one of a Bayesian model, a graph network, a hidden Markov model, a U-net network, or a deep learning network. In some embodiments, determining the second segment associated with the second intraluminal ultrasound image is further based on an outline or location of a guidewire positioned within the first body lumen and visible in the second intraluminal ultrasound image. In some embodiments, determining the second segment associated with the second intraluminal ultrasound image is further based on segmentation of a skeletal feature of the body of the patient visible in the second intraluminal ultrasound image. In some embodiments, determining the second segment associated with the second intraluminal ultrasound image is further based on contours for body lumens that branch from the first body lumen and are visible in the second intraluminal ultrasound image. In some embodiments, the first body lumen properties or the second body lumen properties include at least one of contour area, minimum diameter, maximum diameter, contour eccentricity, contour center location, a shortest distance between body lumens, a number of body lumens visible, a type of body lumens visible, or a change of any of these between the first and second intraluminal ultrasound image. In some embodiments, the model is trained or derived from a mean and standard deviation of at least one of the first body lumen properties for a given vein segment. In some embodiments, the model is trained or derived from one or more annotated images, textbook data, or a library of stored images. In some embodiments, the first body lumen is a peripheral vein, and where the plurality of segments includes at least one of an inferior vena cava (IVC), a confluence, a common iliac vein (CIV), a branch, an external iliac vein (EIV), or a common femoral vein (CFV). Implementations of the described techniques may include hardware, a method or process, or computer software on a computer-accessible medium.

One general aspect includes an intraluminal ultrasound imaging method, which includes receiving, at a processor circuit in communication with an intraluminal ultrasound imaging catheter, a first intraluminal ultrasound image obtained by the intraluminal ultrasound imaging catheter while the intraluminal ultrasound imaging catheter is positioned within a first body lumen of a patient, the first body lumen including a plurality of segments, where the first intraluminal ultrasound image is associated with a first segment of the plurality of segments, and where first intraluminal ultrasound image includes images of the first body lumen and a second body lumen, where the first body lumen includes a first set of first body lumen properties, where the second body lumen includes a first set of second body lumen properties; receiving a second intraluminal ultrasound image obtained by the intraluminal ultrasound imaging catheter while the intraluminal ultrasound imaging catheter is moving at a pullback speed within the first body lumen of the patient, where the second intraluminal ultrasound image includes depictions of the first body lumen and the second body lumen; computing, from the second intraluminal ultrasound image, a second set of first body lumen properties and a second set of second body lumen properties determining a second segment of the plurality of segments associated with the second intraluminal ultrasound image based on a model, where the model is associated with at least one of first set of first body lumen properties, the first set of second body lumen properties, the second set of first body lumen properties, the second set of second body lumen properties, or the pullback speed; and outputting an indication of the second segment or second subsegment to a display in communication with the processor circuit. Other embodiments of this aspect include corresponding computer systems, apparatus, and computer programs recorded on one or more computer storage devices, each configured to perform the actions of the methods.

Implementations may include one or more of the following features. In some embodiments, the method further including displaying, on a display device in communication with the processor circuit, a schematic view of the first body lumen of the patient, where the schematic view includes: the plurality of segments; and a visual indication of the second segment. In some embodiments, the model includes a state transition matrix and at least one of a Bayesian model, a graph network, a hidden Markov model, a U-net network, or a deep learning network. In some embodiments, determining the second segment associated with the second intraluminal ultrasound image is further based on at least one of: an outline or location of a guidewire positioned within the first body lumen and visible in the second intraluminal ultrasound image, segmentation of a skeletal feature of the body of the patient visible in the second intraluminal ultrasound image, or contours for body lumens that branch from the first body lumen and are visible in the second intraluminal ultrasound image. In some embodiments, the first body lumen properties or the second body lumen properties include at least one of contour area, minimum diameter, maximum diameter, contour eccentricity, contour center location, a shortest distance between body lumens, a number of body lumens visible, a type of body lumens visible, or a change of any of these between the first and second intraluminal ultrasound image. In some embodiments, the model is trained or derived from at least one of a mean and standard deviation of at least some of the first body lumen properties for a given vein segment, one or more annotated images, textbook data, or a library of stored images. In some embodiments, the first body lumen is a peripheral vein, and where the plurality of segments includes at least one of an inferior vena cava (IVC), a confluence, a common iliac vein (CIV), a branch, an external iliac vein (EIV), or a common femoral vein (CFV). Implementations of the described techniques may include hardware, a method or process, or computer software on a computer-accessible medium.

One general aspect includes an intravascular ultrasound (IVUS) imaging system for use in peripheral vasculature. The intravascular ultrasound includes an IVUS imaging catheter configured to obtain IVUS images while the IVUS imaging catheter is positioned within a first peripheral blood vessel of a patient, the first peripheral blood vessel including a plurality of segments and subsegments; a processor circuit configured for communication with the IVUS imaging catheter and a display, where the processor circuit is configured to: receive a first IVUS image obtained by the IVUS imaging catheter while the IVUS imaging catheter is positioned within the first peripheral blood vessel of the patient, the first peripheral blood vessel including a plurality of segments and subsegments, where the first IVUS image is associated with a first segment and first subsegment of the plurality of segments and subsegments, and where first IVUS includes depictions of the first peripheral blood vessel and a second peripheral blood vessel, where the first peripheral blood vessel includes a first set of first vessel properties, where the second peripheral blood vessel includes a first set of second blood vessel properties; receive a second IVUS image obtained by the IVUS imaging catheter while the IVUS imaging catheter is moving at a pullback speed within the first peripheral blood vessel of the patient, where the second IVUS image includes depictions of the first peripheral blood vessel and the second peripheral blood vessel; compute, from the second IVUS image, a second set of first vessel properties and a second set of second vessel properties; determine a second segment and second subsegment of the plurality of segments and subsegments associated with the second IVUS image based on a probabilistic model and at least one of first set of first blood vessel properties, the first set of second blood vessel properties, the second set of first vessel properties, the second set of second vessel properties, or the pullback speed; and output an indication of the second segment or second subsegment to the display. Other embodiments of this aspect include corresponding computer systems, apparatus, and computer programs recorded on one or more computer storage devices, each configured to perform the actions of the methods.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the IVUS pullback virtual venogram system, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which.

DETAILED DESCRIPTION

Figure 1:
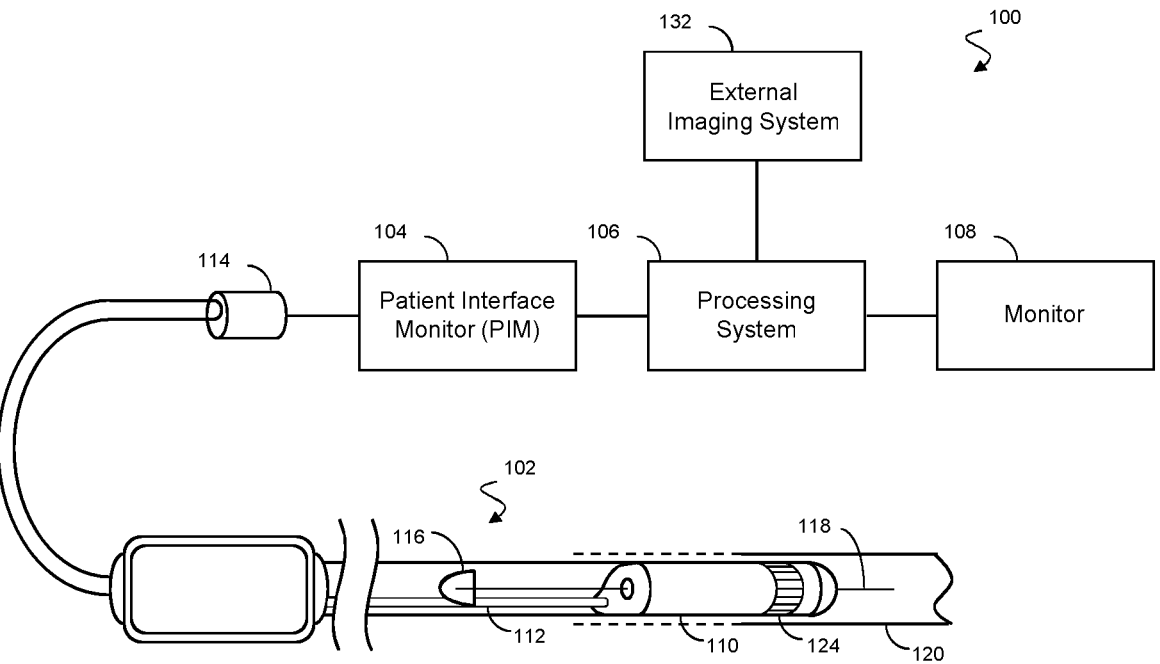
FIG. 1 is a diagrammatic schematic view of an intraluminal imaging system, according to aspects of the present disclosure.

The present disclosure relates generally to medical imaging, including imaging associated with a body lumen of a patient using an intraluminal imaging device. For example, the present disclosure describes systems, devices, and methods for the automatic identification of blood vessel segments in a sequence of IVUS images. This may reduce the need for X-ray images, thus reducing radiation dose for both the patient and the practitioner. It may also reduce the need for manual vessel segment identification, thus reducing the time and attention burden on the clinician or clinical team. This automatic identification relies on landmarks that are identified from the IVUS images by computer vision algorithms, which may for example include machine learning or other pattern recognition algorithms. These landmarks may then be evaluated by a probabilistic algorithm such as a Bayesian graph network, which matches them against a priori anatomical knowledge to identify the correct vein segment of each IVUS image frame.

The present disclosure therefore includes medical image analysis techniques that may include one or more of deep learning, hidden Markov models, Bayesian or other probabilistic models, or time series modeling, and may be applied in image guided therapy, image guided interventions, and other areas.

In a clinical environment, peripheral deep venous interventions use imaging techniques such as X-ray and intravascular ultrasound to assess clinically important chronic iliac vein obstruction, evaluate post-thrombotic disease, locate and assess lesion sites, and to guide and check the placement and deployment of stents. A necessary part of this procedure is the identification of named vein segments (e.g. common iliac vein, inferior vena cava) in the IVUS and/or X-ray images. This is currently done by hand, often using a combination of X-ray and IVUS. The present disclosure enables the automatic identification of vein segments or other vessel or body lumen segments in the IVUS image, without a need for X-ray images or manual segment identification.

The burden reduction acts on multiple levels. First, in current systems the precise identification of vein segments and segment transitions requires taking an additional X-ray image, and pausing (or even reversing) the pull-back of the IVUS catheter. Further, manual annotations have to be made on the spot. This requires frequent use of X-ray, which is a second disadvantage with present systems. It is known that exposure to such radiation is damaging, not just to the patient but also (and perhaps more so) to the clinician and staff who are working with X-ray throughout the day, on many days throughout the course of a career.

The present disclosure overcomes such disadvantages by deriving the required vein segment localization directly from the sequence of images acquired during one smooth IVUS pullback, without the need for slowing down, manual annotation, or added X-ray dose.

The devices, systems, and methods disclosed herein can involve a probabilistic graph model that describes, at the highest level, the vein segment state of the system (i.e. the location of the tip or imaging sensor of the IVUS catheter). Practically, this tip may be in the following states or locations: Inferior Vena Cava, Confluence, Common Iliac Vein, Branch, External Iliac Vein, Common Femoral Vein (and possibly Great Saphenous Vein). Each of these states may be further subdivided into smaller mini states, indicating the relative position (beginning, middle, end) in the vein segment.

At t=0 (e.g., the first IVUS image frame in the pullback), the probability for the system to be in a given state or mini state is set for each state or mini state. This probability may depend on knowledge about the pullback (e.g. it may always start in the Inferior Vena Cava, or at another location specified by a user). At each time step (e.g., for each new frame), the system may stay in the same state or location, or may transition to another state or location; the probability of each state transition is coded in a state transition matrix.

Each IVUS frame may be analyzed by a number of image analysis algorithms (e.g., deep learning or DL algorithms). The output of this analysis can include segmentation results for the vein (or other body lumen), for 0, 1 or 2 arteries that may be present running parallel to the vein, and for a guidewire that may be present inside the vein. Numerical features are derived from these segmentation results. Such features can include vein and artery cross-sectional area/diameter, artery position (or absence), wire presence and position, and other shape and location features for vein, artery and wire. Features may also be dynamic, such as the time (frame-to-frame) gradient of vein area or the movement of an artery towards or away from the vein.

The expected values for each of these features are expressed per vein segment, in the form of a probability distribution with segment-specific parameters. These parameters can be preset from literature, or they can be derived (i.e. the model can be optimized) from observed values in IVUS pullbacks, or a combination of both.

A further feature that may be derived from the image frames is the speed with which the catheter is moved (or in other words, the distance in millimeters between two consecutive frames). This feature, unlike the other features, is not checked against segment-specific expected values, but rather serves to adapt the transition matrix that governs the systems progression from state to state (a higher speed means faster progression).

Once all model parameters are set, a new observation (pullback, series of IVUS frames) can be analyzed by the model to calculate the most likely state sequence (i.e. identification of vein segment per frame) to have generated the observation. The frame positions of vein segment start/stops are read from this state sequence and fed back to the user, e.g. as bookmarks in the series of IVUS images or in a longitudinal view of the complete IVUS pullback. In an example, these features may be incorporated into existing IVUS software and systems.

The present disclosure substantially aids a clinician in labeling vessel segments, by calculating or identifying the most probable segment for each image in a pullback sequence. Implemented on a medical imaging console (e.g., an intraluminal imaging console) in communication with a medical imaging sensor (e.g., an intraluminal ultrasound sensor), the vessel segmentation system disclosed herein provides both time savings and an improvement in the location certainty of captured images. This improved imaging workflow transforms raw imaging data into annotated cross-sectional and longitudinal images and anatomical measurements, without the normally routine need to slow or pause the pullback, acquire X-ray images, or manually identify vessel segments. This unconventional approach improves the functioning of the medical imaging console and sensor, by permitting more efficient workflow and more useful clinical outputs.

The vessel segmentation system may be implemented as a set of logical branches and mathematical operations, whose outputs are viewable on a display, and operated by a control process executing on a processor that can accept user inputs from a keyboard, mouse, or touchscreen interface, and that is in communication with one or more medical imaging sensors (e.g., intraluminal ultrasound sensors). In that regard, the control process performs certain specific operations in response to different sensor inputs and user actions. Certain structures, functions, and operations of the processor, display, sensors, and user input systems are known in the art, while others are recited herein to enable novel features or aspects of the present disclosure with particularity. The vessel segmentation system may include a graphical representation of the vessel, along with vein and artery segmentation information.

These descriptions are provided for exemplary purposes only, and should not be considered to limit the scope of the disclosure. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal imaging system incorporating the IVUS pullback virtual venogram system, according to aspects of the present disclosure. The intraluminal imaging system 100 can be an intravascular ultrasound (IVUS) imaging system in some embodiments. The intraluminal imaging system 100 may include an intraluminal device 102, a patient interface module (PIM) 104, a console or processing system 106, a monitor 108, and an external imaging system 132 which may include angiography, ultrasound, X-ray, computed tomography (CT), magnetic resonance imaging (MRI), or other imaging technologies, equipment, and methods. The intraluminal device 102 is sized and shaped, and/or otherwise structurally arranged to be positioned within a body lumen of a patient. For example, the intraluminal device 102 can be a catheter, guide wire, guide catheter, pressure wire, and/or flow wire in various embodiments. In some circumstances, the system 100 may include additional elements and/or may be implemented without one or more of the elements illustrated in FIG. 1. For example, the system 100 may omit the external imaging system 132.

The intraluminal imaging system 100 (or intravascular imaging system) can be any type of imaging system suitable for use in the lumens or vasculature of a patient. In some embodiments, the intraluminal imaging system 100 is an intraluminal ultrasound (IVUS) imaging system. In other embodiments, the intraluminal imaging system 100 may include systems configured for forward looking intraluminal ultrasound (FL-IVUS) imaging, intraluminal photoacoustic (IVPA) imaging, intracardiac echocardiography (ICE), transesophageal echocardiography (TEE), and/or other suitable imaging modalities.

It is understood that the system 100 and/or device 102 can be configured to obtain any suitable intraluminal imaging data. In some embodiments, the device 102 may include an imaging component of any suitable imaging modality, such as optical imaging, optical coherence tomography (OCT), etc. In some embodiments, the device 102 may include any suitable non-imaging component, including a pressure sensor, a flow sensor, a temperature sensor, an optical fiber, a reflector, a mirror, a prism, an ablation element, a radio frequency (RF) electrode, a conductor, or combinations thereof. Generally, the device 102 can include an imaging element to obtain intraluminal imaging data associated with the lumen 120. The device 102 may be sized and shaped (and/or configured) for insertion into a vessel or lumen 120 of the patient.

The system 100 may be deployed in a catheterization laboratory having a control room. The processing system 106 may be located in the control room. Optionally, the processing system 106 may be located elsewhere, such as in the catheterization laboratory itself. The catheterization laboratory may include a sterile field while its associated control room may or may not be sterile depending on the procedure to be performed and/or on the health care facility.

The catheterization laboratory and control room may be used to perform any number of medical imaging procedures such as angiography, fluoroscopy, CT, IVUS, virtual histology (VH), forward looking IVUS (FL-IVUS), intraluminal photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intraluminal palpography, transesophageal ultrasound, fluoroscopy, and other medical imaging modalities, or combinations thereof. In some embodiments, device 102 may be controlled from a remote location such as the control room, such than an operator is not required to be in close proximity to the patient.

The intraluminal device 102, PIM 104, monitor 108, and external imaging system 132 may be communicatively coupled directly or indirectly to the processing system 106. These elements may be communicatively coupled to the medical processing system 106 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The processing system 106 may be communicatively coupled to one or more data networks, e.g., a TCP/IP-based local area network (LAN). In other embodiments, different protocols may be utilized such as Synchronous Optical Networking (SONET). In some cases, the processing system 106 may be communicatively coupled to a wide area network (WAN). The processing system 106 may utilize network connectivity to access various resources. For example, the processing system 106 may communicate with a Digital Imaging and Communications in Medicine (DICOM) system, a Picture Archiving and Communication System (PACS), and/or a Hospital Information System via a network connection.

At a high level, an ultrasound imaging intraluminal device 102 emits ultrasonic energy from a transducer array 124 included in scanner assembly 110 mounted near a distal end of the intraluminal device 102. The ultrasonic energy is reflected by tissue structures in the medium (such as a lumen 120) surrounding the scanner assembly 110, and the ultrasound echo signals are received by the transducer array 124. The scanner assembly 110 generates electrical signal(s) representative of the ultrasound echoes. The scanner assembly 110 can include one or more single ultrasound transducers and/or a transducer array 124 in any suitable configuration, such as a planar array, a curved array, a circumferential array, an annular array, etc. For example, the scanner assembly 110 can be a one-dimensional array or a two-dimensional array in some instances. In some instances, the scanner assembly 110 can be a rotational ultrasound device. The active area of the scanner assembly 110 can include one or more transducer materials and/or one or more segments of ultrasound elements (e.g., one or more rows, one or more columns, and/or one or more orientations) that can be uniformly or independently controlled and activated. The active area of the scanner assembly 110 can be patterned or structured in various basic or complex geometries. The scanner assembly 110 can be disposed in a side-looking orientation (e.g., ultrasonic energy emitted perpendicular and/or orthogonal to the longitudinal axis of the intraluminal device 102) and/or a forward-looking looking orientation (e.g., ultrasonic energy emitted parallel to and/or along the longitudinal axis). In some instances, the scanner assembly 110 is structurally arranged to emit and/or receive ultrasonic energy at an oblique angle relative to the longitudinal axis, in a proximal or distal direction. In some embodiments, ultrasonic energy emission can be electronically steered by selective triggering of one or more transducer elements of the scanner assembly 110.

The ultrasound transducer(s) of the scanner assembly 110 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In an embodiment the ultrasound transducer array 124 can include any suitable number of individual transducer elements or acoustic elements between 1 acoustic element and 1000 acoustic elements, including values such as 2 acoustic elements, 4 acoustic elements, 36 acoustic elements, 64 acoustic elements, 128 acoustic elements, 500 acoustic elements, 812 acoustic elements, and/or other values both larger and smaller.

The PIM 104 transfers the received echo signals to the processing system 106 where the ultrasound image (including the flow information) is reconstructed and displayed on the monitor 108. The console or processing system 106 can include a processor and a memory. The processing system 106 may be operable to facilitate the features of the intraluminal imaging system 100 described herein. For example, the processor can execute computer readable instructions stored on the non-transitory tangible computer readable medium.

The PIM 104 facilitates communication of signals between the processing system 106 and the scanner assembly 110 included in the intraluminal device 102. This communication may include providing commands to integrated circuit controller chip(s) within the intraluminal device 102, selecting particular element(s) on the transducer array 124 to be used for transmit and receive, providing the transmit trigger signals to the integrated circuit controller chip(s) to activate the transmitter circuitry to generate an electrical pulse to excite the selected transducer array element(s), and/or accepting amplified echo signals received from the selected transducer array element(s) via amplifiers included on the integrated circuit controller chip(s). In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the intraluminal device 102 including circuitry within the scanner assembly 110.

The processing system 106 receives echo data from the scanner assembly 110 by way of the PIM 104 and processes the data to reconstruct an image of the tissue structures in the medium surrounding the scanner assembly 110. Generally, the device 102 can be utilized within any suitable anatomy and/or body lumen of the patient. The processing system 106 outputs image data such that an image of the vessel or lumen 120, such as a cross-sectional IVUS image of the lumen 120, is displayed on the monitor 108. Lumen 120 may represent fluid filled or fluid-surrounded structures, both natural and man-made. Lumen 120 may be within a body of a patient. Lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

The controller or processing system 106 may include a processing circuit having one or more processors in communication with memory and/or other suitable tangible computer readable storage media. The controller or processing system 106 may be configured to carry out one or more aspects of the present disclosure. In some embodiments, the processing system 106 and the monitor 108 are separate components. In other embodiments, the processing system 106 and the monitor 108 are integrated in a single component. For example, the system 100 can include a touch screen device, including a housing having a touch screen display and a processor. The system 100 can include any suitable input device, such as a touch sensitive pad or touch screen display, keyboard/mouse, joystick, button, etc., for a user to select options shown on the monitor 108. The processing system 106, the monitor 108, the input device, and/or combinations thereof can be referenced as a controller of the system 100. The controller can be in communication with the device 102, the PIM 104, the processing system 106, the monitor 108, the input device, and/or other components of the system 100.

In some embodiments, the intraluminal device 102 includes some features similar to traditional solid-state IVUS catheters, such as the EagleEye® catheter available from Philips and those disclosed in U.S. Pat. No. 7,846,101 hereby incorporated by reference in its entirety. For example, the intraluminal device 102 may include the scanner assembly 110 near a distal end of the intraluminal device 102 and a transmission line bundle 112 extending along the longitudinal body of the intraluminal device 102. The cable or transmission line bundle 112 can include a plurality of conductors, including one, two, three, four, five, six, seven, or more conductors.

The transmission line bundle 112 terminates in a PIM connector 114 at a proximal end of the intraluminal device 102. The PIM connector 114 electrically couples the transmission line bundle 112 to the PIM 104 and physically couples the intraluminal device 102 to the PIM 104. In an embodiment, the intraluminal device 102 further includes a guidewire exit port 116. Accordingly, in some instances the intraluminal device 102 is a rapid-exchange catheter. The guidewire exit port 116 allows a guidewire 118 to be inserted towards the distal end in order to direct the intraluminal device 102 through the lumen 120.

The monitor 108 may be a display device such as a computer monitor or other type of screen. The monitor 108 may be used to display selectable prompts, instructions, and visualizations of imaging data to a user. In some embodiments, the monitor 108 may be used to provide a procedure-specific workflow to a user to complete an intraluminal imaging procedure. A processor circuit can be configured to generate the screen displays and output display data to the monitor 108 to display the screen displays.

The external imaging system 132 can be configured to obtain x-ray, radiographic, angiographic/venographic (e.g., with contrast), and/or fluoroscopic (e.g., without contrast) images of the body of a patient (including the vessel 120). External imaging system 132 may also be configured to obtain computed tomography images of the body of patient (including the vessel 120). The external imaging system 132 may include an external ultrasound probe configured to obtain ultrasound images of the body of the patient (including the vessel 120) while positioned outside the body. In some embodiments, the system 100 includes other imaging modality systems (e.g., MRI) to obtain images of the body of the patient (including the vessel 120). The processing system 106 can utilize the images of the body of the patient in conjunction with the intraluminal images obtained by the intraluminal device 102.

Figure 2:
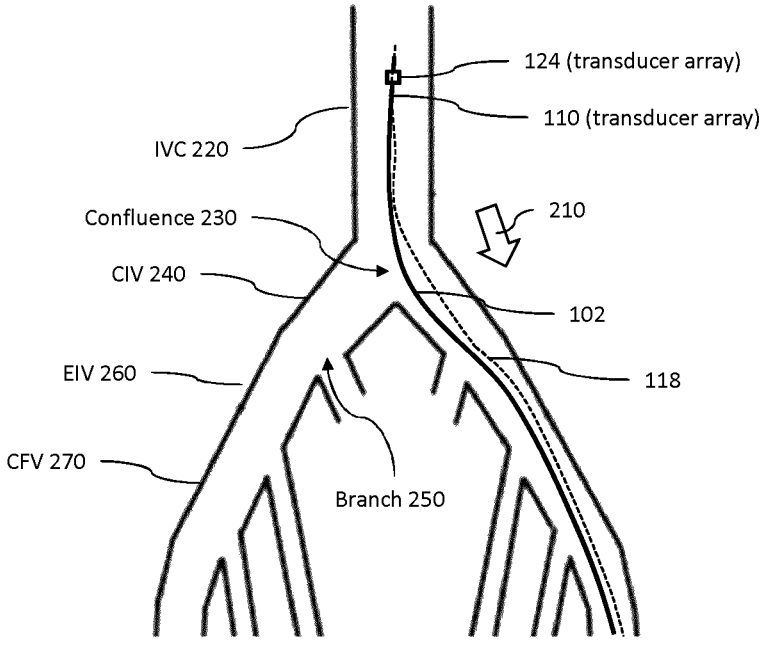
FIG. 2 illustrates veins in the human body, in accordance with at least one embodiment of the present disclosure.

FIG. 2 illustrates veins in the human body, in accordance with at least one embodiment of the present disclosure. For example, veins of the lower torso and legs are shown and labeled. For example, the labeling can be representative of vein segments that are recognized in art. Aspects of the present disclosure can be related to peripheral vasculature, e.g., veins in the torso or legs. Visible are the inferior vena cava (IVC) 220, left and right common iliac vein (CIV) 240, left and right external iliac vein (EIV) 260, and left and right common femoral vein (CFV) 270. Also visible is a confluence 230, where the IVC 220 splits into the left and right common iliac veins 240, and several branches 250, where minor veins branch off from the major (labeled) veins.

Also visible is an intraluminal device 102 such as an IVUS catheter, which includes a scanner assembly 110 that includes a transducer array 124. The intraluminal device 102 may for example be inserted by a clinician and then pulled back (e.g., along a pullback direction 210) at a steady rate to gather images or other data from the interior of the veins. The insertion and/or pullback of the catheter 102 may be aided by a guidewire 118.

Various types of intraluminal imaging systems are used in diagnosing and treating diseases. For example, intravascular ultrasound (IVUS) imaging is used as a diagnostic tool for visualizing vessels within a body of a patient. This may aid in assessing diseased or compressed vessels, such as arteries or veins, within the human body to determine the need for treatment, to optimize treatment, and/or to assess a treatment's effectiveness (e.g., through imaging of the vessel before and after treatment).

In some cases, intraluminal imaging is carried out with an IVUS device including one or more ultrasound transducers. The IVUS device may be passed into the vessel and guided to the area to be imaged. The transducers emit ultrasonic energy and receive ultrasound echoes reflected from the vessel. The ultrasound echoes are processed to create an image of the vessel of interest. The image of the vessel of interest may include one or more lesions or blockages in the vessel and/or sites of narrowing by compression. A stent may be placed within the vessel to treat these blockages or narrowings, and intraluminal imaging may be carried out to view the placement of the stent within the vessel. Other types of treatment include thrombectomy, ablation, angioplasty, pharmaceuticals, etc.

Understanding what artery or vessel segment a particular IVUS frame belongs to can be challenging and time consuming, especially because physicians may see only the cross-sectional IVUS images and a reconstructed longitudinal view (image longitudinal display or ILD) on the dedicated IVUS screen, without any anatomical reference (bony landmarks) to which they can refer. To understand the position of the IVUS probe with respect to the patient's anatomy, physicians currently look at a fluoroscopy X-ray image during pullback. Moreover, during peripheral vascular interventions, the anatomical references for the segments' boundaries are confluences and branches with other vessels, which physicians and other users recognize on IVUS while doing pullbacks, and which they must mentally memorize. Clinicians may also call out regions of interest to be marked by their aides who may be less expert.

Figure 3:
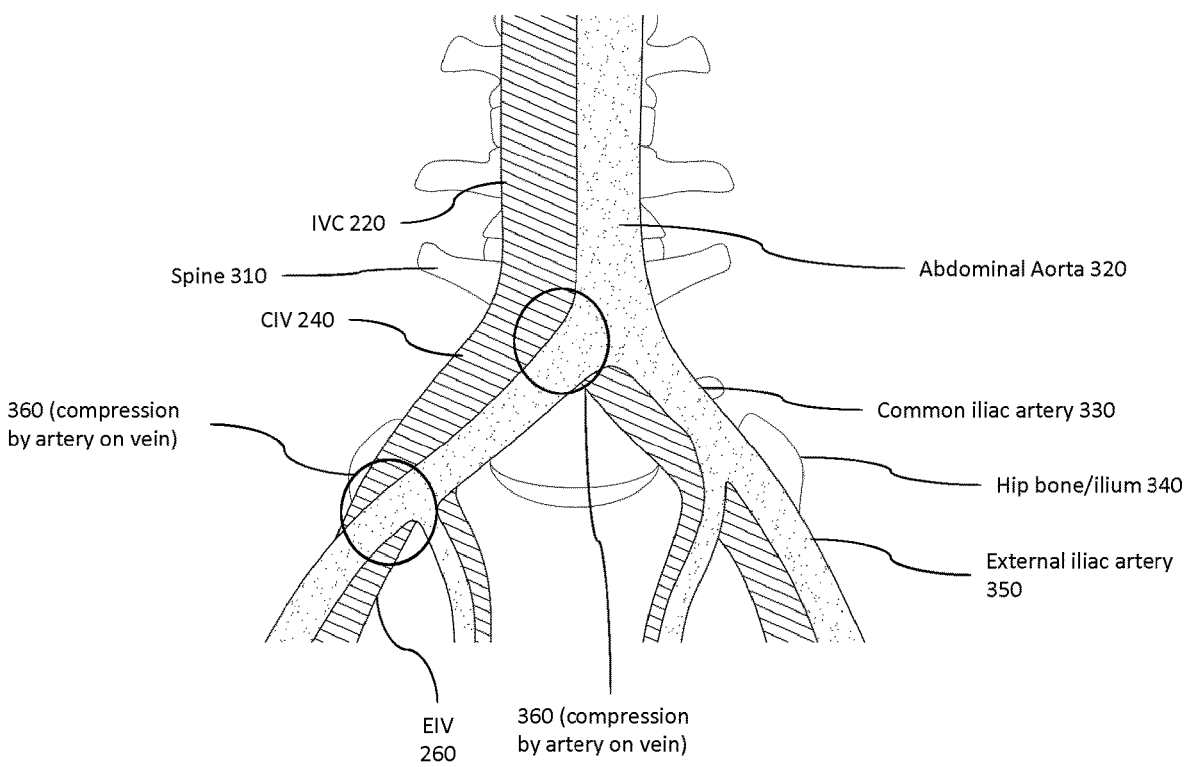
FIG. 3 illustrates blood vessels (e.g., arteries and veins) in the human body, in accordance with at least one embodiment of the present disclosure.

FIG. 3 illustrates blood vessels (e.g., arteries and veins) in the human body, in accordance with at least one embodiment of the present disclosure. For example, veins of the human body are labeled. Aspects of the present disclosure can be related to peripheral vasculature, e.g., veins and arteries in the torso or legs. Visible are the inferior vena cava (IVC) 220, common iliac vein (CIV) 240, external iliac vein (EIV) 260, abdominal aorta 320, common iliac artery 330, and external iliac artery 350. Also visible are the spine 310, hip bone or ilium 340, and two compressions 360 where an artery presses against a vein, distorting the shape of the vein. Any of these listed anatomical features, including shapes and relative positions thereof, may be used for example as landmark features for feature identification in an IVUS image.

Figure 4:
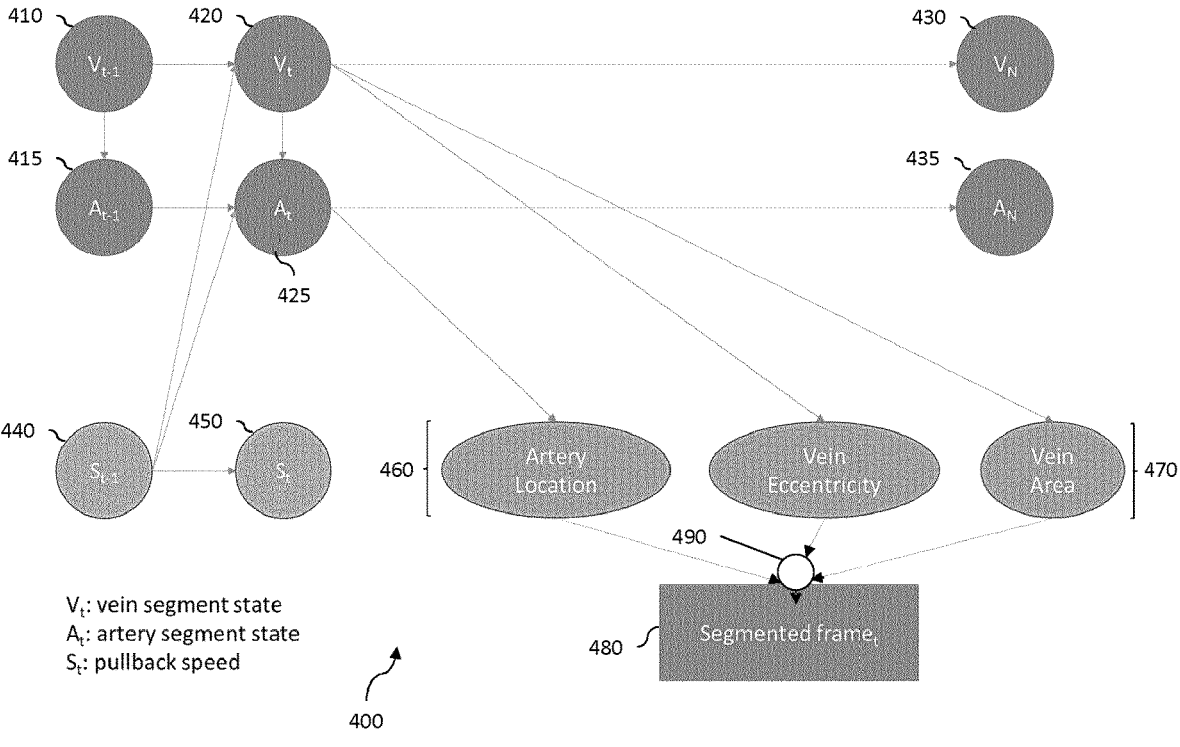
FIG. 4 is a schematic view, in block diagram form, of a method for identifying in which vein segment an imaging probe is currently located, in accordance with at least one embodiment of the present disclosure.

FIG. 4 is a schematic view, in block diagram form, of a method 400 for identifying in which vein segment an imaging probe is currently located, in accordance with at least one embodiment of the present disclosure. In some examples, the method 400 may include a Bayesian graph network. Visible are a vein state (e.g., segment name or abbreviation and/or mini-segment name or abbreviation) 410 at time t−1, and a vein state 420 at time t, and a vein state 430 at time n. Also visible is an artery state 415 at time t−1, an artery state 425 at time t, and an artery state 435 at time n. In an example, the artery may be proximate to the vein, such that it appears in IVUS images taken from within the vein. Also visible is a pullback speed 440 measured or estimated at time t−1, and a pullback speed 450 measured or estimated at time t. In the non-limiting example shown in FIG. 4, the method 400 also includes one or more measured, calculated, or estimated artery properties 460, and one or more measured, calculated, or estimated vein properties 470, which may for example be derived directly or indirectly from the IVUS images generated during the pullback, such that the vein and artery properties at time t are derived from the latest frame or IVUS image available at time t. The output of the method 400 is a segmented frame or IVUS image 480 for time t, which includes an annotation of the name or abbreviation for the most likely current segment.

Arrows indicate dependences: the state 420 of the vein segment state at time t depends on the state 410 at time t−1, while particular values for, for example, vein eccentricity and area (e.g., derived from the segmented frame image at time t) are more likely to be observed under one vein state than under another, e.g. a large vein area is more likely under vein state IVC than under vein state CFV. Note that artery location, vein eccentricity and vein area are merely examples of artery features 460 and vein properties 470, and should not be construed as limiting.

A variety of segmentation algorithms may be employed. In one example, every image frame in the pullback may be analyzed by several deep learning (DL) based segmentation algorithms, including (but not necessarily limited to):

Lumen segmentation: returning the contour of the vein that contains the catheter Artery segmentation: contours for all arteries visible in the frame Non-lumen vein segmentation: contours for veins that split off from the lumen Wire segmentation: outline or location of a guidewire, which may be visible in the Inferior Vena Cava and the Confluence when the IVUS procedure includes accessing the veins of both the left and the right leg Segmentation of the backbone or other skeletal features Each segmentation or detection model can use existing DL methods such as U-net networks. Lumen and artery segmentation may be of particular importance, with other types of landmarks being optional or of lesser importance. The segmentation algorithms may each return sets of coordinates describing the contours, which may then be used to extract features such as: Contour area Minimum/maximum diameter Contour eccentricity Contour center location Shortest distance between e.g. the lumen contour and the closest artery contour Number of arteries visible in a frame time derivatives (e.g., frame to frame differences) of certain features.

A model 490 can then be defined that returns the most likely vein segment for the current frame, resulting in a segmented frame 480. The model 490 can be a mathematical model that mathematically/logically interrelates artery features 460 and/or vein properties 470. In some embodiments, the model 490 is a probabilistic model, a Bayesian model, a graph network, a U-net network, a deep learning network, and/or other suitable mathematical logic. In some embodiments, the model 490 is a hidden Markov model (HMM). An HMM may be seen as a specific type of probabilistic or Bayesian model that is often used to process time series data. In an example, the vein segment likelihood can be derived from two sources.

First, for every segment, a training or definition process gathers sufficient statistics for the features described above. Such statistics may for example be expressed as the mean and standard deviation of all observations of such a feature inside a specific vein segment. To gather these statistics, the process may make use of a library of annotated pullbacks, previously generated and stored, that indicate vein segment start/stops, plus all the previously described vessel contours and other identifiable features. These contours may be generated by a human annotator, or may come from a segmentation algorithm. Descriptions other than mean/standard deviation are possible, such as mean vectors and covariance matrices, non-normal distributions, feature value histograms, or even algorithms trained to learn a feature's likelihood from the gathered data. Arrows between the vein 420 and vessel features (e.g., artery features 460 and vein features 470) describe this dependence.

Second, the likelihood for the intraluminal imaging device (specifically, the transducer array) to be in a certain vein segment at frame t depends on where it was in frame t−1 (indicated by the arrow between elements 410 and 420 (Vt−1 and Vt) in FIG. 4). For example, it is highly unlikely to jump straight from the Inferior Vena Cava to the Common Femoral Vein in a single time step. An HMM or other probabilistic model 490 may therefore include a transition matrix T, that describes the likelihood to jump from one state (vein segment) to the other or to remain in the same state, for all states.

For some embodiments, definition of these two elements is sufficient to define an HMM model or other probabilistic model. However, arteries also run in parallel with the veins that are to be identified, and have named segments of their own. The probabilistic model 490 can therefore be extended with artery states next to the vein states 415, 425, and 435 (At−1, At, An). Such artery states may have their own transition matrix T, and feature statistics can be gathered per artery state as well as per vein state. Artery contour features may therefore be more consistently defined per artery state, whereas lumen features are more homogeneous within a vein state. The lines between artery states At (425) and vein states Vt (420) further indicate that certain combinations of artery and vein are likely, whereas others are unlikely (or even biologically impossible). For example, the Aorta is unlikely to be found next to the CFV.

Figure 5:
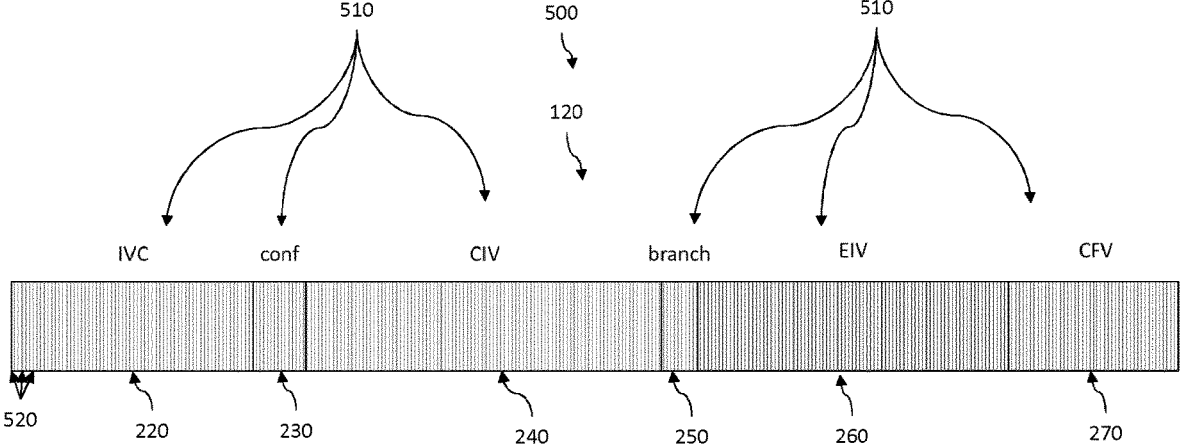
FIG. 5 is a schematic view of a blood vessel or other body lumen, in accordance with at least one embodiment of the present disclosure.

FIG. 5 is a schematic view 500 of a blood vessel or other body lumen 120, in accordance with at least one embodiment of the present disclosure. The schematic view shows division of the lumen 120 into segments 510, and division of each segment into a plurality of sub-segments 520, indicated by the vertical bars in the figure. The number of sub-segments 520 per segment 510 is derived from a priori knowledge of the length of each segment and an estimate or indication of pullback speed.

Typically, the catheter would stay in the same vein segment 510 for a number of frames (say 50-100) before it moves to the next, simply because it needs time to traverse the segment. This time is defined by segment length in mm and the speed with which the catheter is pulled back. To incorporate the known typical lengths of the vein segments 510, each segment 510 is divided into a number of much smaller sub-segments 520. In an example, each sub-segment is one millimeter in length, although other lengths both larger and smaller may be used instead or in addition. The number of the subsegments per frame is directly proportional to a priori (e.g. textbook) knowledge of segment length, and inversely proportional to estimated pullback speed (e.g., a faster pullback will traverse the same distance over fewer frames). Feature statistics can still be gathered per complete, large segment 510: in that case, each of the large segment's sub-segments 520 in the probabilistic model would use the same feature means and variance to evaluate the contour features in each frame. Alternatively, some or all features may be assigned different means for different sub-segments within the same segment, when such features have a known variation over the full segment. For example, the guidewire or a recently branched off vein may be visible in the first (most cranial) sub-segments of the CIV, but not in the more caudal sub-segments.

The transition matrix T can now be defined as a function of probability. For example, if the number of sub-segments 520 is twice the number of image frames in a pullback sequence, and the sub-segments 520 are numbered from left to right 0 .... N, then the most likely state transition from any sub-segment n can be defined as a step to sub-segment n+2, for any n. That means that if the vein segment sequence estimation would depend only on the transition matrix (i.e. in the absence of IVUS image information), this sequence would include only transitions of step 2: 0, 2, 4, ..., N. Such a sequence would have the same relative division into (sub-) segments as chosen in FIG. 5, e.g., it would adhere to the a priori knowledge of segment lengths. Such choices may be appropriate where little or no image information is available to the probabilistic model.

State transitions from n to n+1, n+3 or to n (remaining in the same sub-segment) or n−1 (going back) can be allowed, but with a lower likelihood. This facilitates the interaction between observed image features and a priori knowledge: state transitions other than steps of 2 may be taken, but only if that leads to a higher likelihood of the observed image features in the current frame.

Figures 6A, 6B:
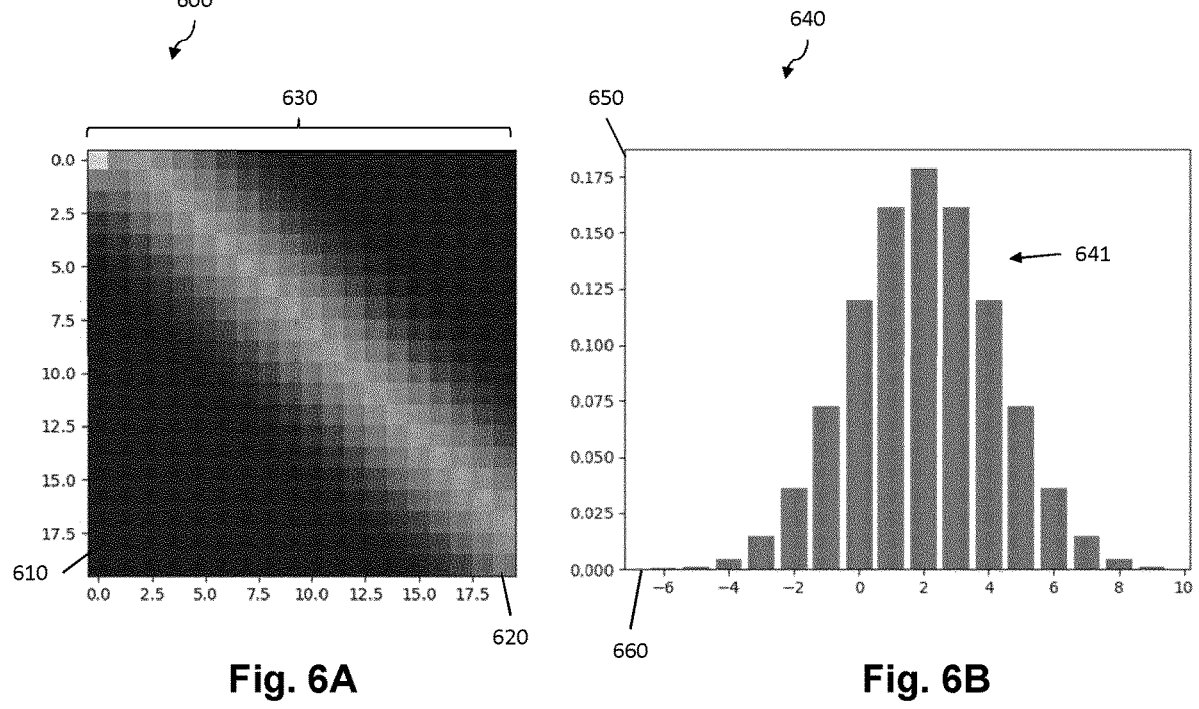
FIG. 6A is a graphical view of a state transition matrix, in accordance with at least one embodiment of the present disclosure.
FIG. 6B is a histogram showing the probability of traversing a given distance between one frame and the next, in accordance with at least one embodiment of the present disclosure.

FIG. 6A is a graphical view of a state transition matrix 600, in accordance with at least one embodiment of the present disclosure. The state transition matrix 600, as described above in FIG. 5, may be chosen as a matrix of rows 610 and columns 620, containing a plurality of state transition probabilities 630. In the example of FIG. 6A, state transition matrix 630 is a band diagonal matrix, wherein higher state transition probabilities 630 are indicated with a brighter color, and lower state transition probabilities are indicated with a darker color. In this example, the row number of each state transition probability indicates the sub-segment number in which the intraluminal imaging device is located at a given time t, and the highest value along that row indicates the most probable sub-segment number for the next time point t+1, based on the motion of the intraluminal imaging device through the body lumen.

FIG. 6B is a histogram 640 showing the probability of traversing a given distance between one frame and the next, in accordance with at least one embodiment of the present disclosure. The histogram 640 may for example show the probable net movements represented by a row 610 of the state transition matrix 600 from FIG. 6A. In this example, the x-axis 660 indicates a distance traveled from time t to time t+1, and the y-axis 650 indicates probability. Thus, the height of each bar 641 in the histogram 640 indicates the transition likelihood for a given distance. In this example, the highest likelihood is at 2, representing a state transition from state n to n+2 between time t and time t+1. For simplicity or computational efficiency, values beyond the band from n−6 to n+9 (or any other desired threshold range) may be set to zero.

In some embodiments, a pullback-speed-dependent transition matrix may also be used to enhance the probabilistic model 490. The transition matrix described above assumes a constant pullback speed, reflected in a uniform most likely state transition of (for example) n to n+2, meaning the intraluminal imaging device moves two sub-segments (e.g., two millimeters) between one frame or time step and the subsequent frame or time step. However, if pullback speed estimations are available, they can also be reflected in the state transition matrix. Higher pullback speeds mean that larger state transition steps (skipping more sub-segments) are likely, which would be implemented as a shift to the right of the values in FIG. 6B (e.g., making a step of 4 rather than 2 the most likely). Similarly, an indication of the intraluminal imaging device (e.g., a catheter or guidewire) standing still would favor a step of zero, while pushbacks (catheter reversing direction) would favor a negative step such as −1.

Pullback speed estimations are available for each frame in the pullback. The transition matrix therefore becomes time/frame dependent. Every state transition from state Vt−1 to Vt now depends on transition matrix Tt−1 which itself is a function of the estimated pullback speed St−1. This now time-dependent state transition matrix can still be used in the probabilistic model calculations as before, with no further adaptations necessarily required.

Figure 7:
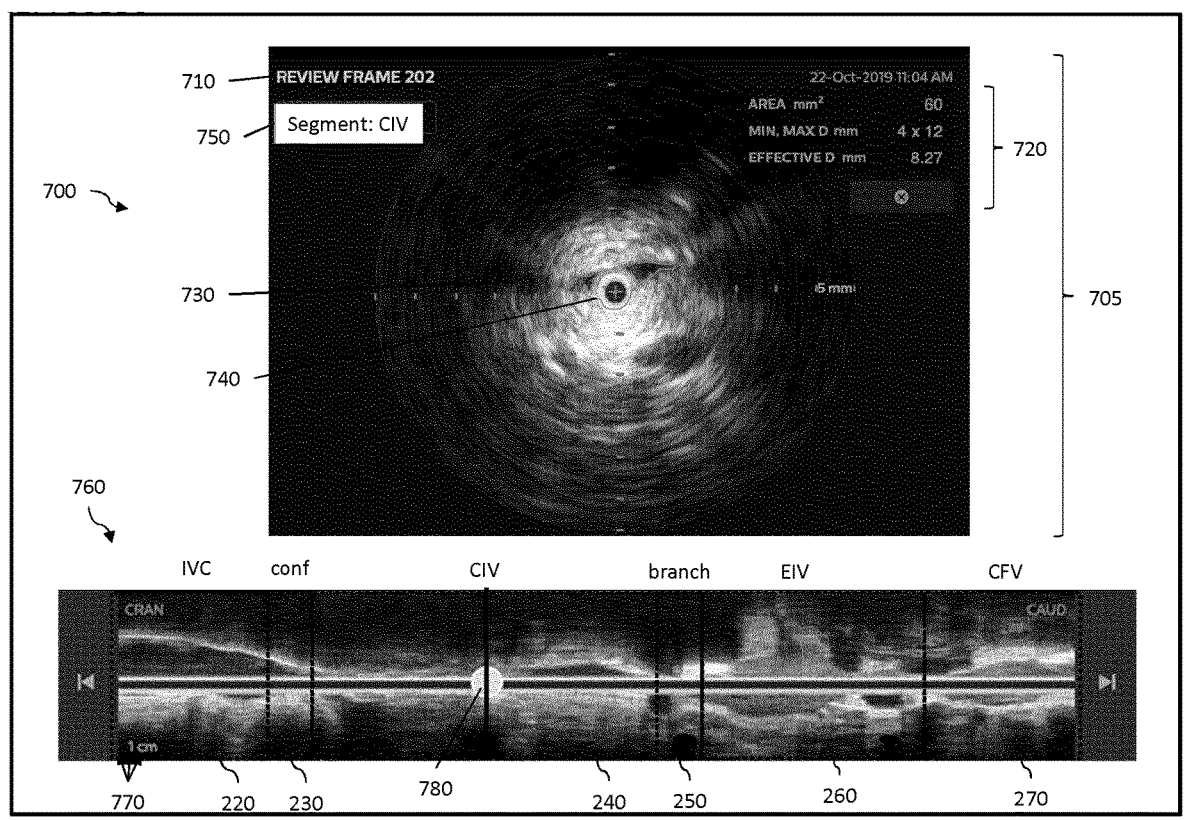
FIG. 7 is an example screen display according to at least one embodiment of the present disclosure.

FIG. 7 is an example screen display 700 according to at least one embodiment of the present disclosure. The screen display 700 includes a cross-sectional image window 705 featuring an intraluminal sensor image 730 (e.g., an IVUS image). Additionally, the cross-sectional image window 705 includes a frame number 710 and an identified segment name or abbreviation 750 (which may for example be the segment name or abbreviation identified by the method 400 of FIG. 4). The cross-sectional image window 705 also includes an automatically mapped contour 740 of the vessel border, which has been used to derive vessel statistics 720. The screen display 700 may for example portray the recorded data after a pullback procedure, or partial data obtained during a pullback.

Examples of border detection, image processing, image analysis, and/or pattern recognition include U.S. Pat. No. 6,200,268 entitled "VASCULAR PLAQUE CHARACTER- IZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety.

In the example shown in FIG. 7, the screen display 700 also optionally includes a longitudinal image 760 made up of a plurality of cross-sectional images 770. The longitudinal image 760 shows the IVC 220, confluence 230, CIV 240, branch 250, EIV 260, and CFV 270. In some embodiments, a pullback may be performed twice on the same vein (or other body lumen): once to acquire a longitudinal image and then again to acquire detailed information at selected points of interest. In such cases, the system may place and move a position indicator or "scrubber" 780 on the longitudinal image 760 based on the current position of the intraluminal imaging device as determined above in FIGS. 4-6. In other examples, the details are examined in the post-procedure recording, and the scrubber or position indicator 780 can be put at the exact frame position corresponding to the image 700, rather than physically performing a second pullback. In some embodiments, the probabilistic model may be trained or derived from an annotated version of the longitudinal image, rather than from textbook data or a library of stored images.

Figure 8:
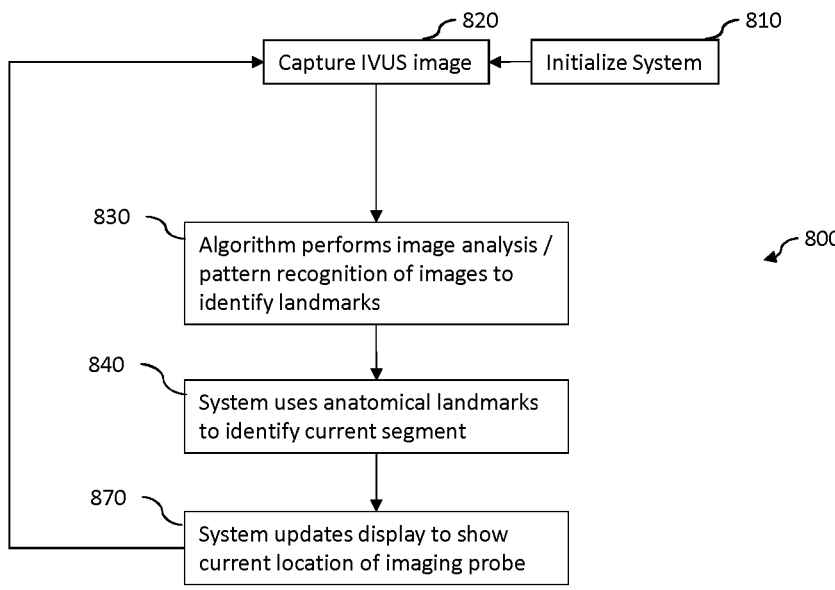
FIG. 8 illustrates a flow diagram for an example intraluminal directional guidance method, in accordance with aspects of the present disclosure.

FIG. 8 illustrates a flow diagram for an example intraluminal directional guidance method 800, in accordance with aspects of the present disclosure. It is understood that the steps of method 800 may be performed in a different order than shown in FIG. 8, additional steps can be provided before, during, and after the steps, and/or some of the steps described can be replaced or eliminated in other embodiments. These steps may be executed for example as coded instructions on a processor such as processing system 106 of FIG. 1 or processor circuit 950 of FIG. 9, and displayed for example on monitor 108 of FIG. 1, in response to inputs by a clinician or other user. Depending on the implementation, these steps may be performed in real time or near-real time during a pullback procedure, or may be performed after the procedure using recorded data, or combinations thereof.

In step 810, the system is initialized and prepared for imaging. In an example, the intraluminal device has been inserted into the vessel of interest and is ready to begin the imaging procedure. In some embodiments, the user may initialize the IVUS imaging system with directional information at the start of the procedure (e.g., an IVUS pullback procedure), such as entry point or access point into the body (e.g., right or left femoral vein) and the target anatomy or direction of movement. This information may be used by the system to select specific algorithms, data sets, or body regions for image recognition. In other embodiments, no user inputs are necessary.

In step 820, the IVUS imaging system 100 captures an IVUS image. Such images may be captured either discretely or continuously during a procedure (e.g., a pullback procedure), and stored within a memory of the processing system 106.

In step 830, the processor 106 performs border detection, image processing, image analysis, and pattern recognition of the captured IVUS image to identify anatomical landmarks (e.g., specific veins and arteries, branching points between veins or arteries, bones, instruments, etc.). While the pullback run is performed, the algorithm detects these landmarks as described above in FIGS. 4-6.

In step 840, the processor identifies the segment in which the IVUS imaging probe is most likely currently located, as described above in FIGS. 4-6.

In step 870, the processing system updates the display to show the name of the segment in which the probe is currently located, and/or stores the current segment name in memory along with the current IVUS image frame. Execution then returns to step 820. In some embodiments where the method is performed on recorded data, the display may be updated only once, to show all segment labels.

A person or ordinary skill in the art will understand that for some embodiments, one or more of the above steps could be eliminated or performed in a different sequence, and that other steps may be added.

Collectively, the features described above enable the system to group and label all IVUS frames between landmarks as belonging to a particular named segment of the patient's vasculature. The system accordingly auto computes the relevant metrics for diagnosis for that segment, e.g. compression, highlights areas of attention, and indicates the relative anatomical position of an IVUS frame.

Figure 9:
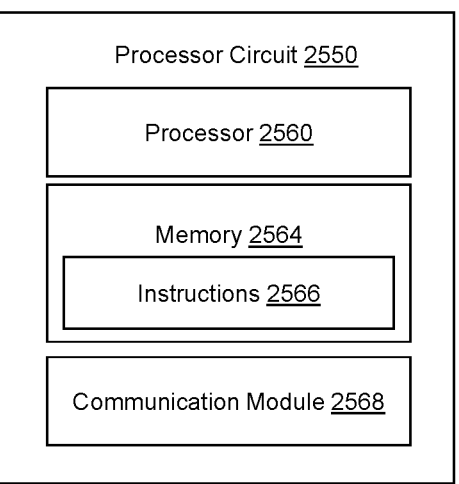
FIG. 9 is a schematic diagram of a processor circuit, according to embodiments of the present disclosure.

FIG. 9 is a schematic diagram of a processor circuit 950, according to embodiments of the present disclosure. The processor circuit 950 may be implemented in the ultrasound imaging system 100, or other devices or workstations (e.g., third-party workstations, network routers, etc.), or in a cloud processor or other remote processing unit, as necessary to implement the method. As shown, the processor circuit 950 may include a processor 960, a memory 964, and a communication module 968. These elements may be in direct or indirect communication with each other, for example via one or more buses.

The processor 960 may include a central processing unit (CPU), a digital signal processor (DSP), an ASIC, a controller, or any combination of general-purpose computing devices, reduced instruction set computing (RISC) devices, application-specific integrated circuits (ASICs), field programmable gate arrays (FPGAs), or other related logic devices, including mechanical and quantum computers. The processor 960 may also comprise another hardware device, a firmware device, or any combination thereof configured to perform the operations described herein. The processor 960 may also be implemented as a combination of computing devices, e.g., a combination of a DSP and a microprocessor, a plurality of microprocessors, one or more microprocessors in conjunction with a DSP core, or any other such configuration.

The memory 964 may include a cache memory (e.g., a cache memory of the processor 960), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 964 includes a non-transitory computer-readable medium. The memory 964 may store instructions 966. The instructions 966 may include instructions that, when executed by the processor 960, cause the processor 960 to perform the operations described herein. Instructions 966 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 968 can include any electronic circuitry and/or logic circuitry to facilitate direct or indirect communication of data between the processor circuit 950, and other processors or devices. In that regard, the communication module 968 can be an input/output (I/O) device. In some instances, the communication module 968 facilitates direct or indirect communication between various elements of the processor circuit 950 and/or the ultrasound imaging system 100. The communication module 968 may communicate within the processor circuit 950 through numerous methods or protocols. Serial communication protocols may include but are not limited to US SPI, I²C, RS-232, RS-485, CAN, Ethernet, ARINC 429, MODBUS, MIL-STD-1553, or any other suitable method or protocol. Parallel protocols include but are not limited to ISA, ATA, SCSI, PCI, IEEE-488, IEEE-1284, and other suitable protocols. Where appropriate, serial and parallel communications may be bridged by a UART, USART, or other appropriate subsystem.

External communication (including but not limited to software updates, firmware updates, preset sharing between the processor and central server, or readings from the ultrasound device) may be accomplished using any suitable wireless or wired communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. For example, a Bluetooth Low Energy (BLE) radio can be used to establish connectivity with a cloud service, for transmission of data, and for receipt of software patches. The controller may be configured to communicate with a remote server, or a local device such as a laptop, tablet, or handheld device, or may include a display capable of showing status variables and other information. Information may also be transferred on physical media 610 such as a USB flash drive or memory stick.

A number of variations are possible on the examples and embodiments described above. For example, the vessel identification system may be employed in anatomical systems within the body other than those described, or may be employed to image other disease types, object types, or procedure types than those described. The technology described herein may be applied to intraluminal imaging sensors of diverse types, whether currently in existence or hereinafter developed. For example, any system including an automatic method for vein segment detection may be considered to employ the techniques described herein, if the vein segments appear automatically on the user's screen during or after IVUS acquisition, without manual intervention. The present disclosure may be applied in the field of IVUS for image guided intervention. Further applications can be thought of in any field where images are collected by a moving sensor along a trajectory from A to B, where at least some a priori knowledge is available about the trajectory and the expected observations/measurements per predefined subtrajectory.

In some embodiments, common use of the devices, methods, and systems disclosed herein would act on a complete (e.g., recorded) sequence of images. This may involve using the full set of pullback frames, or partial pullbacks (including a sequence of partial pullbacks, each time from frame 1 to the current, 'live' frame). Although not using the full pullback may not provide optimal results, it is technically possible using the same methods, model and even largely the same code as the option where the full pullback is used. In some cases, the optimal use of the proposed model would be to act on the complete sequence of IVUS images and produce the complete segment detection output after completion of the pullback, rather than producing a segment prediction after every frame.

The logical operations making up the embodiments of the technology described herein are referred to variously as operations, steps, objects, elements, components, or modules. Furthermore, it should be understood that these may be performed in any order, unless explicitly claimed otherwise or a specific order is inherently necessitated by the claim language. All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the vessel segmentation system. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or" rather than "exclusive or." Unless otherwise noted in the claims, stated values shall be interpreted as illustrative only and shall not be taken to be limiting.

The above specification, examples and data provide a complete description of the structure and use of exemplary embodiments of the vessel segmentation system as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter. Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An apparatus, comprising:

an intravascular imaging catheter configured for intravascular ultrasound (IVUS) or optical coherence tomography; and a processor circuit configured for communication with the intravascular imaging catheter, wherein the processor circuit is configured to:

control the intravascular imaging catheter to obtain a plurality of intravascular images during a pullback through a plurality of vein segments, wherein the plurality of intravascular images comprises a first intravascular image, wherein the plurality of vein segments comprises a first vein segment;

determine a plurality of anatomical features for the plurality of intravascular images;

represent the plurality of vein segments as a plurality of states in a probabilistic model comprising:

a likelihood that the plurality of states comprises the plurality of anatomical features;

a likelihood of transitioning between the plurality of states during the pullback;

identify, based on the probabilistic model, a first state of the plurality of states as most probable for the first intravascular image;

determine, based on the first state representing the first vein segment, that the intravascular imaging catheter was located in the first vein segment when the first intravascular image was obtained; and output, to a display in communication with the processor circuit, a screen display comprising the first intravascular image and an indication of the first vein segment.

2. The apparatus of claim 1, wherein the processor circuit is configured to:

divide each vein segment into a plurality of subsegments; and represent each subsegment as a distinct state in the probabilistic model.

3. The apparatus of claim 2, wherein the processor circuit is configured to determine a quantity of the plurality of subsegments for each vein segment based on a speed of the pullback and a length of each vein segment.

4. The apparatus of claim 1, wherein the plurality of anatomical features comprises at least two of: vein cross-sectional area, vein diameter, vein eccentricity, artery position, guidewire presence, or distance between vein and artery.

5. The apparatus of claim 1, wherein at least one of the plurality of anatomical features is time-dependent such that the processor circuit is configured to determine at least one of a gradient of vein area or artery movement.

6. The apparatus of claim 1, wherein, to determine the plurality of anatomical features, the processor circuit is configured to segment the plurality of intravascular images using a deep learning network distinct from the probabilistic model.

7. The apparatus of claim 1, wherein the probabilistic model comprises a Hidden Markov Model.

8. The apparatus of claim 1, wherein the processor circuit is configured to define the likelihood that the plurality of states comprises the plurality of anatomical features based on a set of vein segment-specific probability distributions.

9. The apparatus of claim 8, wherein the processor circuit is configured to define the likelihood of transitioning between the plurality of states based on a transition matrix.

10. The apparatus of claim 9, wherein the processor circuit is configured to adjust the transition matrix based on a speed of the pullback.

11. The apparatus of claim 1, wherein the processor circuit is configured to represent a plurality of artery segments as a plurality of artery states in the probabilistic model, wherein the plurality of artery segments is proximate to the plurality of vein segments such that the probabilistic model comprises dependencies between:

the plurality of artery states; and the plurality of states representing the plurality of vein segments.

12. The apparatus of claim 1, wherein the plurality of intravascular images comprises a second intravascular image, wherein the plurality of vein segments comprises a second vein segment, wherein the processor circuit is configured to:

identify, based on the probabilistic model, a second state of the plurality of states as most probable for the second intravascular image;

determine, based on the second state representing the second vein segment, that the intravascular imaging catheter was located in the second vein segment when the second intravascular image was obtained.

13. The apparatus of claim 12, wherein the processor circuit is configured to output a longitudinal view of the plurality of vein segments comprising a plurality of text labels for the plurality of vein segments.

14. The system of claim 1, wherein the plurality of vein segments comprises at least two of: an inferior vena cava (IVC), a confluence, a common iliac vein (CIV), a branch, an external iliac vein (EIV), or a common femoral vein (CFV).

*    *    *    *    *